United States Patent
Alisi et al.

(10) Patent No.: US 9,655,906 B2
(45) Date of Patent: May 23, 2017

(54) TRICYCLIC INDAZOLE COMPOUND, METHOD OF PREPARATION AND PHARMACEUTICAL COMPOSITION CONTAINING IT

(71) Applicant: AZIENDE CHIMICHE RIUNITE ANGELINI FRANCESCO A.C.R.A.F S.p.A., Rome (IT)

(72) Inventors: Maria Alessandra Alisi, Rome (IT); Nicola Cazzolla, Albano Laziale (IT); Guido Furlotti, Rome (IT); Beatrice Garrone, Rome (IT); Gabriele Magaro, Loc. Pavona-Castel Gandolfo (IT); Giorgina Mangano, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 14/803,384

(22) Filed: Jul. 20, 2015

(65) Prior Publication Data

US 2015/0320763 A1    Nov. 12, 2015

Related U.S. Application Data

(62) Division of application No. 13/639,632, filed as application No. PCT/EP2011/053270 on Mar. 4, 2011, now Pat. No. 9,120,801.

(30) Foreign Application Priority Data

Apr. 8, 2010  (EP) .................................... 10159346

(51) Int. Cl.
   *A61K 31/4985*    (2006.01)
   *C07D 487/04*    (2006.01)
   *A61K 31/551*    (2006.01)

(52) U.S. Cl.
   CPC ........ *A61K 31/551* (2013.01); *A61K 31/4985* (2013.01); *C07D 487/04* (2013.01)

(58) Field of Classification Search
   None
   See application file for complete search history.

(56) References Cited

U.S. PATENT DOCUMENTS

2010/0056573 A1    3/2010  Alisi et al.

FOREIGN PATENT DOCUMENTS

| WO | 03 057213 | 7/2003 |
|----|-----------|--------|
| WO | 2006 050803 | 5/2006 |
| WO | 2008 061688 | 5/2009 |

OTHER PUBLICATIONS

Popa, D., et al., "Contribution of 5-$HT_2$ Receptor Subtypes to Sleep-Wakefulness and Respiratory Control and Functional Adaptations in Knock-Out Mice Lacking 5-$HT_{2A}$ Receptors," The Journal of Neuroscience, vol. 25, No. 49, pp. 11231-11238, (Dec. 7, 2005).

(Continued)

*Primary Examiner* — Marcos Sznaidman
*Assistant Examiner* — Rayna B Rodriguez
(74) *Attorney, Agent, or Firm* — Oblon, McClelland, Maier & Neustadt, L.L.P.

(57) ABSTRACT

Tricyclic indazole compound and its pharmaceutically acceptable salts of acid addition, use thereof, method and intermediates for preparing them, and a pharmaceutical composition containing them.

The tricyclic indazole compound has the following general formula (I):

(Continued)

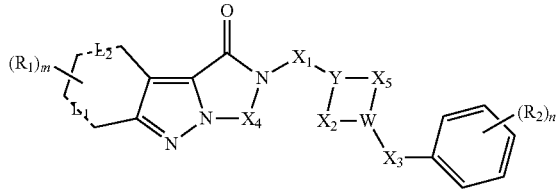

in which
$R_1$, $R_2$, $L_1$, $L_2$, $X_1$, $X_2$, $X_3$, $X_4$, $X_5$, Y, W, m, and n have the meanings stated in the description.

6 Claims, 1 Drawing Sheet

(56) References Cited

OTHER PUBLICATIONS

Kapur, S., et al., "Scrotonin-Dopamine Interaction and Its Relevance to Schizophrenia," American Journal of Psychiatry, vol. 154, No. 4, pp. 466-476, (Apr. 1996).
Van Oekelen, D., et al., "5-$HT_{2A}$ and 5-$HT_{2C}$ receptors and their atypical regulation properties," Life Sciences, vol. 72, No. 22, pp. 2429-2449, (2003).
Briejer, M.R., et al., "5-HT receptor types in the rat ileum longitudinal muscle: focus on 5-$HT_2$ receptors mediating contraction," Neurogastroenterol. Mot., vol. 9, No. 4, pp. 231-237, (1997).
Nagatomo, T., et al., "Functions of 5$HT_{2A}$ receptor and its antagonists in the cardiovascular system," Pharmacology & Therapeutics, vol. 104, No. 1, pp. 59-81, (2004).
May, J.A., et al., "Evaluation of the Ocular Hypotensive Response of Serotonin 5-$HT_{1A}$ and 5-$HT_2$ Receptor Ligands in Conscious Ocular Hypertensive Cynomolgus Monkeys," The Journal of Pharmacology and Experimental Therapeutics, vol. 306, No. 1, pp. 301-309, (2003).
Bonhaus, D.W., et al., "The pharmacology and distribution of human 5-hydroxytryptamine$_{2B}$ (5-$HT_{2B}$) receptor gene products: comparison with 5-$HT_{2A}$ and 5-$HT_{2C}$ receptors," British Journal of Pharmacology, vol. 115, pp. 622-628, (1995).
Cheng, Y.C., et al., "Relationship Between the Inhibition Constant ($K_I$) and the Concentration of Inhibitor Which Causes 50 Per Cent Inhibition ($I_{50}$) of an Enzymatic Reaction," Biochemical Pharmacology, vol. 22, pp. 3099-3108, (1973).
Wolf, W.A., et al., "The Serotonin 5-$HT_{2C}$ Receptor is a Prominent Serotonin Receptor in Basal Ganglia: Evidence from Functional Studies on Serotonin-Mediated Phosphoinositide Hydrolysis," Journal of Neurochemistry, vol. 69, pp. 1449-1458, (1997).
Sztanke, K., et al.; "Antinociceptive activity of new imidazolidine carbonyl derivatives. Part 4. Synthesis and pharmacological activity of 8-aryl-3,4-dioxo-2H,8H-6,7-dihydroimidazo[2,1-c][1,2,4]triazines," European Journal of Medicinal Chemistry, vol. 40, pp. 127-134, (2005).
Corne, S.J., et al., "A Method for Assessing the Effects of Drugs on the Central Actions of 5-Hydroxytryptamine," British Journal of Pharmacology, vol. 20, pp. 106-120, (1963).
International Search Report Issued May 18, 2011 in PCT/EP11/53270 Filed Apr. 4, 2011.
C. Dezi, et al., J. Med. Chem. vol. 50, pp. 32-42-3255 (2007).
R.A. Glennon, "Serotonin Receptor Subtypes and Ligands," in Psychopharmacology—The Fourth Generation of Progress, F. E. Bloom et al., Eds., Raven Press, NY, 1005.
Huff Jr, King SW, Saari WS, Springer JP, Martin GE, and Williams M. Bioactive Conformation of 1-Arylpiperazines at Central Serotonin Receptors, J. Med. Chem. 1985;28:945-948.
Knittel J and Zavod R. Drug Design and Relationship of Functional Groups to Pharmacological Activity; Foye's Principles of Medicinal Chemistry, 5$^{th}$ Edition, Lippincott Williams & Wilkins; ed. David A Williams and Thomas L Lemke; 2002; 37-67.

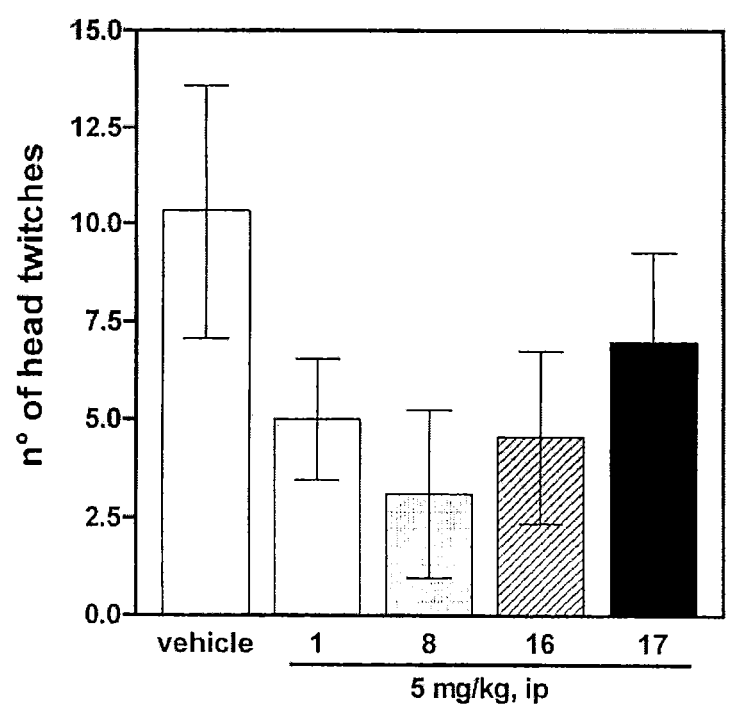

TRICYCLIC INDAZOLE COMPOUND, METHOD OF PREPARATION AND PHARMACEUTICAL COMPOSITION CONTAINING IT

CROSS REFERENCES TO RELATED APPLICATIONS

This application is a Divisional Application of U.S. patent application Ser. No. 13/639,632, filed on Oct. 5, 2012, which was a 371 of International Patent Application No. PCT/EP11/53270, filed on Mar. 4, 2011, and claims priority to European Patent Application No. 10159346.5, filed on Apr. 8, 2010.

FIELD OF THE INVENTION

The present invention relates to novel tricyclic indazole compounds, a method and intermediates for the preparation thereof, a pharmaceutical composition containing it, and the use thereof.

In particular, the present invention relates to novel tricyclic indazole compounds having selective affinity for the 5-HT$_{2A}$ receptors, useful in the treatment of some pathologies that involve the 5-HT$_{2A}$ receptors, for example, some disorders of the central nervous system, as well as disorders of the smooth muscles either of the gastrointestinal system or of the cardiovascular system. The activity on said receptors is also useful in regulating intra-ocular pressure and, as consequence, in the treatment of glaucoma.

STATE OF THE ART

The 2A serotonin receptor (5-HT$_{2A}$) is a receptor coupled to protein G, present in many species and widely distributed in the human body. The process of transmission of the signal resulting from receptor activation is not entirely clear. It is known that activation of this receptor, via the protein G coupled to it, leads to the activation of various enzymes such as phospholipase C (with consequent hydrolysis of phosphatidylinositol diphosphate and production of inositol triphosphate) or phospholipase A2 (which leads to the release of arachidonic acid). The receptor response leads, moreover, to a flux of calcium ions (Ca$^{2+}$) into the cell and to activation of functional proteins such as protein kinase C. The receptor is present in the central nervous system, in the cells of the vascular and gastrointestinal smooth muscles and in the platelets.

International patent publication WO2008061688 describes 2-alkyl-indazole compounds having selective activity on 5-HT$_2$ receptors and, with regard to the various receptor subtypes, compounds having preferential affinity on 5-HT$_{2A}$ receptors compared with 5-HT$_{2C}$ receptors.

Other compounds are known to have preferential affinity for the 5-HT$_{2A}$ receptor, such as, for example, pimavanserin (ACP-103) undergoing phase III clinical trials for the treatment of Parkinson's disease psychosis, and eplivanserin (SR46349) and volinanserin (M100907), both undergoing phase III clinical trials for insomnia.

The 5-HT$_{2A}$ receptor are involved in some disorders of the central nervous system, such as, for example, sleep disorders (Popa D. et al., J Neurosci. 2005; 25(49): 11231-11238), schizophrenia (Kapur S et al., Am J Psychiatry. 1996; 153: 466-476) and anxiety (Van Oekelen D et al., Life Sci. 2003; 72(22): 2429-2449) as well as smooth muscles disorders either of the gastrointestinal system (Briejer M R et al., Neurogastroenterol Motil. 1997; 9(4): 231-237) or of the cardiovascular system (Nagatomo T et al., Pharmacol Ther. 2004; 104(1): 59-81).

Moreover, compounds having 5-HT$_{2A}$ receptor selective affinity can be effective in regulating intra-ocular pressure and, as consequence, in the treatment of pathologies such as glaucoma (Jesse A. May et al., J Pharmacol Exp Ther. 2003; 306(1): 301-309).

International patent publication WO2006050803 discloses bi- or tricyclic indazole compounds and salts thereof, for selectively combating harmful plants in cultures of useful plants or for regulating the growth of plants.

SUMMARY OF THE INVENTION

Now, the Applicant has surprisingly found novel tricyclic indazolamide compounds having selective affinity for the 5-HT$_{2A}$ receptor.

Further, the Applicant has found that the novel tricyclic indazolamide compounds have a much lower selective affinity on 5-HT$_{2C}$ receptors compared with 5-HT$_{2A}$ receptors.

This biological activity markedly differs from that of known tricyclic indazole compounds, for example from that described in the above mentioned international patent publication WO 2006050803.

Moreover, the compounds of the present invention have a structure that is notably different from the known compounds having preferential affinity for the 5-HT$_{2A}$ receptor.

The novel tricyclic indazole compounds of the present invention can be useful in the treatment of some pathologies that involve the 5-HT$_{2A}$ receptor, for example some disorders of the central nervous system such as sleep disorders, schizophrenia and anxiety, as well as disorders of the smooth muscles either of the gastrointestinal system, such as irritable bowel syndrome (IBS), chronic constipation, diarrhoea, and functional dyspepsia or of the cardiovascular system, such as hypertension, myocardial ischemia, cerebral ischemia, migraine, thrombosis, and platelet aggregation. The activity on said receptor is also useful in regulating intra-ocular pressure and, as consequence, in the treatment of glaucoma.

Accordingly, a first aspect of the present invention relates to a tricyclic indazole compound of general formula (I):

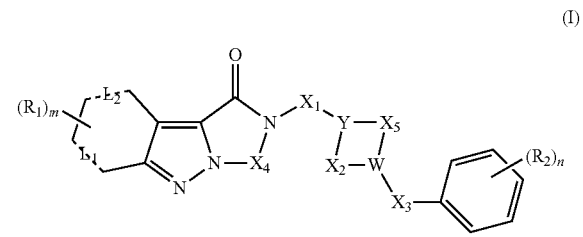

where
Y is CH or N;
W is CH or N;
provided that at least one of Y and W is a nitrogen atom;
X$_1$ and X$_3$ can be independently a σ bond, a divalent alkyl chain containing from 1 to 5 carbon atoms, a carbonyl group, a divalent alkanoyl chain of the type —CO—(CH$_2$)$_{1-4}$— or —(CH$_2$)$_{1-4}$—CO—, wherein the hydrogen atoms of said alkyl and alkanoyl chains can be optionally substituted with one or more halogen atoms, one or more C$_{1-3}$alkyl groups, one or more C$_{1-3}$alkoxy groups;

$X_4$ can be a divalent alkyl chain containing from 1 to 5 carbon atoms, a carbonyl group, a divalent alkanoyl chain of the type —CO—$(CH_2)_{1-4}$— or —$(CH_2)_{1-4}$—CO—, wherein the hydrogen atoms of said alkyl and alkanoyl chains can be optionally substituted with one or more halogen atoms, one or more $C_{1-3}$alkyl groups, one or more $C_{1-3}$alkoxy groups;

$X_2$ and $X_5$ can be independently a σ bond or a divalent alkyl chain containing from 1 to 4 carbon atoms, wherein the hydrogen atoms of said alkyl chain can be optionally substituted with one or more halogen atoms, one or more $C_{1-3}$alkyl groups, one or more $C_{1-3}$alkoxy groups;

$L_1$ and $L_2$ can be independently a σ bond or a π bond;

$R_1$ can be independently H, OH, halogen, CN, $C_{1-3}$alkyl, $C_{1-3}$alkoxy, $NR^iR^{ii}$, $NO_2$, $CF_3$, $CONR^{iii}R^{iv}$, $SO_2R^v$, $OCF_3$, $N(R^{vi})SO_2R^{vii}$, $C(NR^{viii})N(R^{ix}R^x)$, $N(R^{xi})C(O)R^{xii}$;

$R_2$ can be independently H, OH, halogen, CN, $C_{1-3}$alkyl, $C_{1-3}$alkoxy, $C_{1-3}$hydroxyalkyl, $C_{1-3}$aminoalkyl, $NR^iR^{ii}$, $NO_2$, $CF_3$, $CONR^{iii}R^{iv}$, $SO_2R^v$, $OCF_3$, $N(R^{vi})SO_2R^{vii}$, $C(NR^{viii})N(R^{ix}R^x)$, $N(R^{xi})C(O)R^{xii}$;

m and n can be independently from 1 to 3;

$R^i$, $R^{ii}$, $R^{iii}$, $R^{iv}$, $R^v$, $R^{vi}$, $R^{vii}$, $R^{viii}$, $R^{ix}$, $R^x$, $R^{xi}$, $R^{xii}$ can be independently H or $C_{1-3}$alkyl;

and its salts of addition with pharmaceutically acceptable organic and inorganic acids.

Typical examples of pharmaceutically acceptable acids are: oxalic, maleic, methanesulphonic, paratoluenesulphonic, succinic, citric, tartaric, lactic, hydrochloric, phosphoric and sulphuric.

According to a preferred embodiment of the present invention, in the general formula (I) above, $X_1$ can be a carbonyl group, a divalent alkyl chain containing from 1 to 3 carbon atoms, a divalent alkanoyl chain of the type —CO—$(CH_2)_{1-3}$— or —$(CH_2)_{1-3}$—CO—, wherein the hydrogen atoms of said alkyl and alkanoyl chains can be optionally substituted with one or more halogen atoms, or one or more $C_{1-3}$alkyl groups.

According to an even more preferred embodiment of the present invention, in the general formula (I) above, $X_1$ can be —CO—, —$CH_2$—, or —$(CH_2)_3$—.

According to a preferred embodiment of the present invention, in the general formula (I) above, $X_3$ can be a σ bond, a divalent alkyl chain containing from 1 to 3 carbon atoms, a divalent alkanoyl chain of the type —CO—$(CH_2)_{1-2}$—, wherein the hydrogen atoms of said alkyl and alkanoyl chains can be optionally substituted with one or more halogen atoms, or one or more $C_{1-3}$alkyl groups.

According to an even more preferred embodiment of the present invention, in the general formula (I) above, $X_3$ can be a σ bond, —$(CH_2)_2$—, —CO—$CH_2$—, or —$CH_2CF_2$—.

According to a preferred embodiment of the present invention, in the general formula (I) above, $X_4$ can be a divalent alkyl chain containing from 1 to 3 carbon atoms, a divalent alkanoyl chain of the type —CO—$(CH_2)_{1-2}$— or —$(CH_2)_{1-2}$—CO, wherein the hydrogen atoms of said alkyl and alkanoyl chains can be optionally substituted with one or more halogen atoms, or one or more $C_{1-3}$alkyl groups.

According to an even more preferred embodiment of the present invention, in the general formula (I) above, $X_4$ can be —$(CH_2)_2$—, —$(CH_2)_3$—; —$CH_2$—CO—, or —CO—$CH_2$—.

According to a preferred embodiment of the present invention, in the general formula (I) above, $X_2$ and $X_5$ can be a divalent alkyl chain containing from 1 to 3 carbon atoms, wherein the hydrogen atoms of said alkyl and alkanoyl chains can be optionally substituted with one or more halogen atoms, or one or more $C_{1-3}$alkyl groups.

According to an even more preferred embodiment of the present invention, in the general formula (I) above, $X_2$ can be —$(CH_2)_2$—, or —$(CH_2)_3$— and $X_5$ can be —$CH_2$—, or —$(CH_2)_2$—.

According to a preferred embodiment of the present invention, in the general formula (I) above, $L_1$ and $L_2$ can be both a σ bond or both a π bond.

According to a preferred embodiment of the present invention, in the general formula (I) above, $R_1$ can be independently H, OH, F, Cl, CN, $C_{1-3}$alkyl group, $C_{1-3}$alkoxy group, $NR^iR^{ii}$ group, $NO_2$, $CF_3$, $CONR^{iii}R^{iv}$ group, $SO_2R^v$, and $OCF_3$.

According to an even more preferred embodiment of the present invention, in the general formula (I) above, $R_1$ can be independently H, OH, F, CN, $CF_3$, and $CONH_2$.

According to a preferred embodiment of the present invention, in the general formula (I) above, $R_2$ can be independently H, OH, F, Cl, CN, $C_{1-3}$alkyl, $C_{1-3}$alkoxy, $C_{1-3}$hydroxyalkyl, $C_{1-3}$aminoalkyl, $NR^iR^{ii}$, $NO_2$, $CF_3$, $CONR^{iii}R^{iv}$, $SO_2R^v$, $OCF_3$.

According to an even more preferred embodiment of the present invention, in the general formula (I) above, $R_2$ can be independently H, OH, F, $CH_2OH$, $CH_2NH_2$, $CONH_2$;

According to a preferred embodiment of the present invention, in the general formula (I) above, m is 1 and n can be 1 or 2.

A second aspect of the present invention relates to a method for preparing (i) a tricyclic indazole compound of general formula (I) and, optionally (ii) a salt of acid addition thereof with pharmaceutically acceptable inorganic and organic acids.

Accordingly, the method of the present invention, in a first embodiment thereof, is characterized in that it comprises (1b) the condensation of an amide derivative of formula (IV):

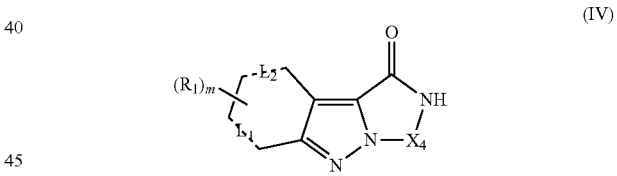

where
$R_1$, $L_1$, $L_2$, $X_4$, and m have the meanings stated previously in relation to the compound of formula (I),
with a derivative of formula (V)

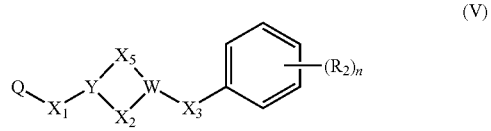

where
$R_2$, $X_1$, $X_2$, $X_3$, $X_5$, W, Y, and n have the meanings stated previously in relation to the compound of formula (I), and
Q is a leaving group selected from the group comprising a halogen atom, a mesylate group ($CH_3SO_3^-$) and a tosylate group (p-MePhSO_3^-),
to give a tricyclic indazole compound of general formula (I).

Preferably, Q is a chlorine atom, a bromine atom or a mesylate group.

Further, the method of the present invention, when W is a nitrogen atom, is characterized in that it comprises (1a) the condensation of an amine of formula (II)

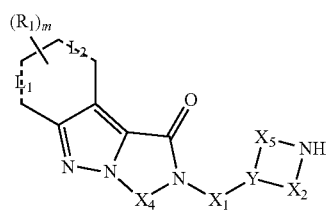
(II)

where
$X_1$, $X_2$, $X_4$, $X_5$, Y, $L_1$, $L_2$, $R_1$ and m have the meanings stated previously in relation to the compound of formula (I), with a derivative of formula (III)

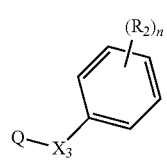
(III)

where
$X_3$, $R_2$ and n have the meanings stated previously in relation to the compound of formula (I), and Q is a leaving group selected from the group comprising a halogen atom, a mesylate group ($CH_3SO_3^-$) and a tosylate group (p-MePhSO$_3^-$), to give a tricyclic indazole derivative of general formula (I).

Preferably, Q is a bromine atom or a mesylate group.

If desired, the tricyclic indazole derivative of general formula (I) is made to react with a pharmaceutically acceptable organic or inorganic acid to give the salt of acid addition thereof.

The condensation step (1b) can be carried out by conventional techniques, in the presence of a base. For example, an amide derivative of formula (IV) is reacted with a compound of formula (V) in which Q is, preferably, a chlorine atom, a bromine atom or a mesylate group, in the presence of a base. Typical example of base is sodium hydride.

Preferably, the condensation step (1b) is carried out in the presence of a diluent at a temperature comprises between −20° C. and the boiling temperature of the solvent and for a time comprised between 0.5 and 48 hours. Preferably, the temperature ranges from 0° C. to the boiling temperature of the solvent. Preferably, the reaction time is from 1 to 24 hours.

Typically, the diluent used is a polar aprotic solvent. Examples of suitable polar aprotic solvents are N,N-dimethylformamide or tetrahydrofuran.

The condensation step (1a) can also be carried out by conventional techniques, preferably in the presence of a base. For example, an amine of formula (II) can be reacted with a compound of formula (III) in which Q is, preferably, a bromine atom or a mesylate group, preferably in the presence of a base. Typical examples of bases are carbonate or bicarbonate of potassium, sodium or caesium.

Preferably, the condensation step (1a) is carried out in the presence of a diluent at a temperature from room temperature (20° C.) to 160° C. and for a time from 1 to 72 hours. Preferably, the reaction temperature ranges from room temperature (20° C.) to 100° C. Preferably, the reaction time is from 12 to 48 hours.

Typically, the diluent used is a protic or aprotic polar solvent. Suitable examples of protic polar solvents are alcohols such as ethanol. Suitable examples of polar aprotic solvents are acetone or N,N-dimethylformamide.

The compound obtained in either in the condensation step (1b) or (1a) can be purified by conventional techniques such as flash chromatography and crystallization.

The tricyclic indazole derivative of general formula (I) obtained with either the condensation step (1b) or (1a) can be made to react with a pharmaceutically acceptable organic or inorganic acid to form the salt of acid addition thereof.

The formation of a salt of acid addition of a tricyclic indazole compound of general formula (I) with a pharmaceutically acceptable organic or inorganic acid can be carried out by conventional techniques.

For example, it can be carried out by first dissolving the compound of formula (I) in a diluent and then treating the solution thus obtained with an organic or aqueous solution of the acid of interest.

Typical examples of diluents are ethanol, isopropanol, ethyl acetate and diethyl ether. The obtained salt can then be separated by conventional techniques and, if applicable, purified by crystallization.

Some intermediates of formula (II) and (IV) are novel, and they therefore constitute a further aspect of the present invention.

Accordingly, in a further aspect, the present invention relates to the intermediate compounds of formula (II):

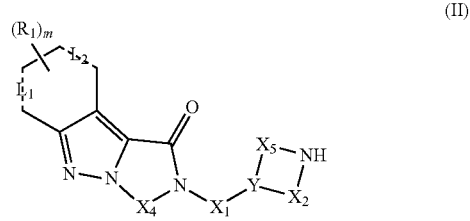
(II)

where
$X_1$, $X_2$, $X_4$, $X_5$, Y, $L_1$, $L_2$, $R_1$ and m have the meanings stated previously in relation to the compound of formula (I);

In a still further aspect, the present invention relates to the intermediate compounds of formula (IV):

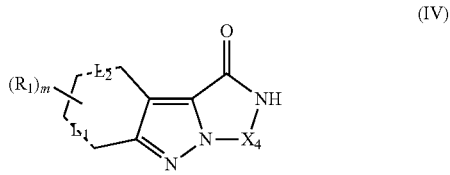
(IV)

where
$R_1$, $L_1$, $L_2$, $X_4$ and m have the meanings stated previously in relation to the compound of formula (I), provided that, when $R_1$ is H and $L_1$ and $L_2$ are π bond, $X_4$ is different from $CH_2CH_2$ or $CH_2CH_2CH_2$, and when $R_1$ is H and $L_1$ and $L_2$ are σ bond, $X_4$ is different from $CH_2CH_2$.

The amine of formula (II) as well as the tricyclic derivatives of formula (IV) can be prepared by conventional methods, for example as described in scheme 1.

Successively, the protective group $P_1$ is removed and the resulting primary amine is intra-molecular reacted with the ester group, to give the cyclic amine of formula (IV).

The latter is alkylated by reaction with the alkylating agent of formula (IX), where $Q_2$ indicates a leaving group Scheme 1

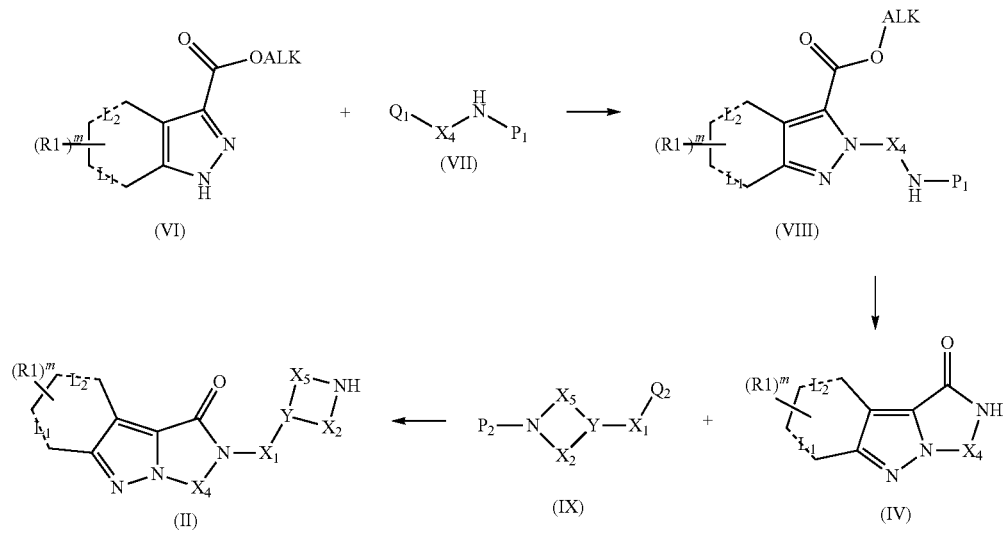

The synthetic pattern provides, as first step, an alkylation of indazole-carboxylic acid ester derivative of formula (VI) by means of the alkylating agent of formula (VII), where $Q_1$ indicates a leaving group selected from the group comprising a halogen atom, a mesylate group ($CH_3SO_3^-$) and a tosylate group (p-MePhSO$_3^-$), and $P_1$ indicates a protective group of terminal amines selected from the group comprising 9-fluorenylmethyl carbamate (Fmoc), tert-butyl carbamate (Boc) and N-benzylidenamine. Preferably, $Q_1$ is a chlorine atom, a bromine atom or a mesylate group.

selected from the group comprising a halogen atom, a mesylate group ($CH_3SO_3^-$) and a tosylate group (p-MePhSO$_3^-$) and $P_2$ indicates a protective group of terminal amines selected from the group comprising 9-fluorenylmethyl carbamate (Fmoc) and tert-butyl carbamate (Boc). Preferably, $Q_2$ is a chlorine atom, a bromine atom or a mesylate group.

Successively, the protective group $P_2$ is removed to form the amine derivatives of formula (II).

The compounds exemplified in the following Table 1 can be prepared by the synthetic pattern described above.

TABLE 1

| No. | $L_1$ | $L_2$ | R1 | R2 | X1 | $X_2$ | $X_3$ | $X_4$ | $X_5$ | Y | W | m | n |
|---|---|---|---|---|---|---|---|---|---|---|---|---|---|
| 1 | π | π | H | p-F | $CH_2$ | $(CH_2)_2$ | $(CH_2)_2$ | $(CH_2)_2$ | $(CH_2)_2$ | CH | N | 1 | 1 |
| 2 | π | π | H | H | $CH_2$ | $(CH_2)_3$ | $(CH_2)_2$ | $(CH_2)_2$ | $CH_2$ | CH | N | 1 | 1 |
| 3 | π | π | 7-F | o-F | $CH_2$ | $(CH_2)_2$ | $(CH_2)_2$ | $(CH_2)_2$ | $(CH_2)_2$ | CH | N | 1 | 1 |
| 4 | π | π | 7-CN | o-F | $CH_2$ | $(CH_2)_2$ | $(CH_2)_2$ | $(CH_2)_2$ | $(CH_2)_2$ | CH | N | 1 | 1 |
| 5 | π | π | H | o-F | $CH_2$ | $(CH_2)_3$ | $(CH_2)_2$ | $(CH_2)_2$ | $CH_2$ | CH | N | 1 | 1 |
| 6 | π | π | 7-CONH$_2$ | o-F | $CH_2$ | $(CH_2)_2$ | $(CH_2)_2$ | $(CH_2)_2$ | $(CH_2)_2$ | CH | N | 1 | 1 |
| 7 | π | π | H | o-F | $CH_2$ | $(CH_2)_2$ | $(CH_2)_2$ | $CH_2CO$ | $(CH_2)_2$ | CH | N | 1 | 1 |
| 8 | π | π | H | o-F | $CH_2$ | $(CH_2)_2$ | $(CH_2)_2$ | $(CH_2)_2$ | $(CH_2)_2$ | CH | N | 1 | 1 |
| 9 | π | π | H | o-F | $CH_2$ | $(CH_2)_2$ | $(CH_2)_2$ | $COCH_2$ | $(CH_2)_2$ | CH | N | 1 | 1 |
| 10 | π | π | H | p-F | $CH_2$ | $(CH_2)_3$ | $(CH_2)_2$ | $(CH_2)_3$ | $CH_2$ | CH | N | 1 | 1 |
| 11 | π | π | H | o-F p-OH | $CH_2$ | $(CH_2)_2$ | $(CH_2)_2$ | $(CH_2)_2$ | $(CH_2)_2$ | CH | N | 1 | 2 |
| 12 | π | π | H | o-F p-CH$_2$OH | $CH_2$ | $(CH_2)_2$ | $(CH_2)_2$ | $(CH_2)_2$ | $(CH_2)_2$ | CH | N | 1 | 2 |
| 13 | π | π | H | o-F | $CH_2$ | $(CH_2)_3$ | $(CH_2)_2$ | $(CH_2)_3$ | $CH_2$ | CH | N | 1 | 1 |
| 14 | π | π | H | o-F p-CH$_2$NH$_2$ | $CH_2$ | $(CH_2)_2$ | $(CH_2)_2$ | $(CH_2)_2$ | $(CH_2)_2$ | CH | N | 1 | 2 |
| 15 | π | π | H | o-F m'-CONH$_2$ | $CH_2$ | $(CH_2)_2$ | $(CH_2)_2$ | $(CH_2)_2$ | $(CH_2)_2$ | CH | N | 1 | 2 |
| 16 | π | π | H | p-F | $CH_2$ | $(CH_2)_2$ | $(CH_2)_2$ | $(CH_2)_3$ | $(CH_2)_2$ | CH | N | 1 | 1 |
| 17 | σ | σ | H | p-F | $CH_2$ | $(CH_2)_2$ | $(CH_2)_2$ | $(CH_2)_2$ | $(CH_2)_2$ | CH | N | 1 | 1 |
| 18 | σ | σ | H | o-F | $CH_2$ | $(CH_2)_2$ | $COCH_2$ | $(CH_2)_2$ | $(CH_2)_2$ | CH | N | 1 | 1 |

TABLE 1-continued

| No. | L₁ | L₂ | R1 | R2 | X1 | X₂ | X₃ | X₄ | X₅ | Y | W | m | n |
|---|---|---|---|---|---|---|---|---|---|---|---|---|---|
| 19 | σ | σ | H | o-F p-OH | CH₂ | (CH₂)₂ | COCH₂ | (CH₂)₂ | (CH₂)₂ | CH | N | 1 | 2 |
| 20 | π | π | H | H | CH₂ | (CH₂)₂ | (CH₂)₂ | (CH₂)₂ | (CH₂)₂ | CH | N | 1 | 1 |
| 21 | π | π | H | o-F m-CONH₂ | CH₂ | (CH₂)₂ | (CH₂)₂ | (CH₂)₂ | (CH₂)₂ | CH | N | 1 | 2 |
| 22 | π | π | H | H | CH₂ | (CH₂)₂ | (CH₂)₂ | (CH₂)₃ | (CH₂)₂ | CH | N | 1 | 1 |
| 23 | π | π | H | o-F | CH₂ | (CH₂)₂ | (CH₂)₂ | (CH₂)₃ | (CH₂)₂ | CH | N | 1 | 1 |
| 24 | π | π | H | p-F | CH₂ | (CH₂)₂ | CH₂CF₂ | (CH₂)₂ | (CH₂)₂ | CH | N | 1 | 1 |
| 25 | π | π | H | H | CH₂ | (CH₂)₂ | COCH₂ | (CH₂)₂ | (CH₂)₂ | CH | N | 1 | 1 |
| 26 | π | π | H | H | CH₂ | (CH₂)₂ | COCH₂ | (CH₂)₃ | (CH₂)₂ | CH | N | 1 | 1 |
| 27 | π | π | H | p-F | CH₂ | (CH₂)₂ | CH₂CF₂ | (CH₂)₃ | (CH₂)₂ | CH | N | 1 | 1 |
| 28 | π | π | H | H | (CH₂)₃ | (CH₂)₂ | σ | (CH₂)₂ | (CH₂)₂ | N | CH | 1 | 1 |
| 29 | π | π | H | H | CH₂ | (CH₂)₂ | CH₂CF₂ | (CH₂)₂ | (CH₂)₂ | CH | N | 1 | 1 |
| 30 | π | π | H | H | CH₂ | (CH₂)₂ | CH₂CF₂ | (CH₂)₃ | (CH₂)₂ | CH | N | 1 | 1 |
| 31 | π | π | H | H | (CH₂)₃ | (CH₂)₂ | σ | (CH₂)₃ | (CH₂)₂ | N | CH | 1 | 1 |
| 32 | π | π | 9-CF₃ | o-F | CH₂ | (CH₂)₂ | (CH₂)₂ | (CH₂)₂ | (CH₂)₂ | CH | N | 1 | 1 |
| 33 | π | π | 8-OH | o-F | CH₂ | (CH₂)₂ | (CH₂)₂ | (CH₂)₂ | (CH₂)₂ | CH | N | 1 | 1 |
| 34 | π | π | H | o-F | CO | (CH₂)₂ | (CH₂)₂ | (CH₂)₂ | (CH₂)₂ | CH | N | 1 | 1 |

Typical examples of pathological states that might benefit from treatment with the novel tricyclic indazole compound of formula (I) having selective affinity for the 5-HT$_{2A}$ receptor are some disorders of the central nervous system, such as, for example, sleep disorders (Popa D. et al., J Neurosci. 2005; 25(49): 11231-11238), schizophrenia (Kapur S et al., Am J Psychiatry. 1996; 153: 466-476) and anxiety (Van Oekelen D et al., Life Sci. 2003; 72(22): 2429-2449) as well as smooth muscles disorders either of the gastrointestinal system (Briejer M R et al., Neurogastroenterol Motil. 1997; 9(4): 231-237) or of the cardiovascular system (Nagatomo T et al., Pharmacol Ther. 2004; 104(1): 59-81). Moreover, said pharmaceutical composition can be effective in regulating intra-ocular pressure and, as consequence, in the treatment of pathologies such as glaucoma (May J A et al., J Pharmacol Exp Ther. 2003; 306(1): 301-309).

Another aspect of the present invention relates to the use of the above described tricyclic indazole compound of general formula (I) or of a salt thereof with a pharmaceutically acceptable organic or inorganic acid, for the preparation of a medicament for the treatment of a pathological state selected from the group consisting of disorders of the central nervous system, disorders of the smooth muscles either of the gastrointestinal system or of the cardiovascular system, and ocular pathologies.

More in particular, the present invention relates to the use of the above described tricyclic indazole compound of general formula (I) or of a salt thereof with a pharmaceutically acceptable organic or inorganic acid, for the preparation of a medicament for the treatment of a disorder of the central nervous system selected from the group consisting of sleep disorders, schizophrenia, and anxiety.

The present invention also relates to the use of the above described tricyclic indazole compound of general formula (I) or of a salt thereof with a pharmaceutically acceptable organic or inorganic acid, for the preparation of a medicament for the treatment of a disorder of the smooth muscles of the gastrointestinal system selected from the group consisting of irritable bowel syndrome (IBS), chronic constipation, diarrhoea, and functional dyspepsia.

The present invention also relates to the use of the above described tricyclic indazole compound of general formula (I) or of a salt thereof with a pharmaceutically acceptable organic or inorganic acid, for the preparation of a medicament for the treatment of a disorder of the smooth muscles of the cardiovascular system selected from the group consisting of hypertension, myocardial ischemia, cerebral ischemia, migraine, thrombosis, and platelet aggregation.

The present invention also relates to the use of the above described tricyclic indazole compound of general formula (I) or of a salt thereof with a pharmaceutically acceptable organic or inorganic acid, for the preparation of a medicament for the treatment of glaucoma.

The present invention further relates to a method for the treatment of a pathological state selected from the group comprising disorders of the central nervous system, disorders of the smooth muscles either of the gastrointestinal system or of the cardiovascular system, and ocular pathologies comprising the administration in a patient in need thereof of a therapeutically effective amount of at least one tricyclic indazole compound of formula (I) as described above or of a salt thereof with a pharmaceutically acceptable organic or inorganic acid.

In particular, disorders of the central nervous system which can be treated with the method of the present invention are sleep disorders, schizophrenia, and anxiety.

Disorders of the smooth muscles of the gastrointestinal system which can be treated with the method of the present invention are irritable bowel syndrome (IBS), chronic constipation, diarrhoea, and functional dyspepsia.

Disorders of the smooth muscles of the cardiovascular system which can be treated with the method of the present invention are hypertension, myocardial ischemia, cerebral ischemia, migraine, thrombosis, and platelet aggregation.

Ocular pathologies which can be treated with the method of the present invention are glaucoma.

A further aspect of the present invention relates to a pharmaceutical composition comprising an effective amount of at least one tricyclic indazole compound of formula (I) as described above or of a salt thereof with a pharmaceutically acceptable organic or inorganic acid and at least one inert pharmaceutically acceptable excipient.

Preferably, the pharmaceutical composition of the present invention is prepared in suitable dosage forms comprising an effective amount of at least one tricyclic indazole compound of formula (I) as described above or of a salt thereof with a pharmaceutically acceptable organic or inorganic acid and at least one inert pharmaceutically acceptable excipient.

Therefore, a further aspect of the present invention relates to the use of the aforementioned pharmaceutical composition for treating a pathological state selected from the group comprising disorders of the central nervous system such as sleep disorders, schizophrenia, and anxiety, disorders of the smooth muscles either of the gastrointestinal system, such as irritable bowel syndrome (IBS), chronic constipation, diarrhoea, and functional dyspepsia or of the cardiovascular system, such as hypertension, myocardial ischemia, cerebral ischemia, migraine, thrombosis, and platelet aggregation, and ocular pathologies such as glaucoma.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions.

Other suitable dosage forms are those with sustained release and those based on liposomes for oral, injectable or transdermal administration.

The dosage forms can also contain other traditional ingredients such as: preservatives, stabilizers, surfactants, buffers, salts for regulating osmotic pressure, emulsifiers, sweeteners, colorants, flavourings and the like.

If required by special therapeutic requirements, the pharmaceutical composition of the present invention can contain other pharmacologically active ingredients, whose simultaneous administration is useful.

The amount of the tricyclic indazole compound of formula (I) or of the pharmaceutically acceptable salt of acid addition thereof in the pharmaceutical composition of the present invention can vary over a wide range depending on known factors, for example, the type of pathology, the severity of the disease, the patient's body weight, the dosage form, the chosen route of administration, the number of administrations per day and the efficacy of the selected tricyclic indazole compound of formula (I). However, a person skilled in the art can determine the optimum amount in easily and routinely manner.

Typically, the amount of tricyclic indazole compound of formula (I) or of the pharmaceutically acceptable salt of acid addition thereof in the pharmaceutical composition of the present invention will be such as to ensure a level of administration from 0.0001 to 100 mg/kg/day. Preferably, the level of administration is from 0.001 to 50 mg/kg/day, and even more preferably from 0.01 to 10 mg/kg/day.

The dosage forms of the pharmaceutical composition of the present invention can be prepared by techniques that are familiar to a pharmaceutical chemist, and comprise mixing, granulation, compression, dissolution, sterilization and the like.

The description that follows is intended for further illustration of the present invention, though without limiting it.

SHORT DESCRIPTION OF THE FIGURE

FIG. 1 is a graphic showing the effect of tested compounds following intraperitoneal administration on head twitch test in mice according to the procedure of the Test C described hereinbelow. On the Y axis, the number of head twitches following the intraperitoneal administration of the compounds indicated on the X axis, are reported.

EXPERIMENTAL PART $^1$H-NMR spectroscopy: a) Varian Gemini 200 (200 MHz) b) Brucker 300 Avance (300 MHz); internal standard=trimethylsilane. [(s)=singlet; (d)=doublet; (t)=triplet; (q)=quartet; (qn)=quintuplet; (sxt)=sextuplet; (spt)=septuplet; (bs)=broad singlet; (bd)=broad doublet; (dd)=double doublet; (dt)=double triplet; (tt)=triple triplet; (m)=multiplet; J=coupling constant; δ=chemical shift (in ppm)].

Example 1

2-({1-[2-(4-fluorophenyl)ethyl]piperidin-4-yl}methyl)-3,4-dihydropyrazino[1,2-b]indazol-1(2H)-one hydrochloride 1a) Methyl of 2-(2-chlorethyl)-2H-indazole-3-carboxylate 1-bromo-2-chlorethane (70 ml; 0.84 mol) was added slowly to a suspension of methyl ester of 1H(2H)-indazole-3-carboxylic acid (20 g; 0.084 mol), caesium carbonate (24.4 g; 0.177 mol) in acetonitrile (600 ml) kept stirred at room temperature. The reaction mixture was kept under stirring at the same temperature for 3 days, then the solid was removed by filtration. The solvent was removed by evaporation at reduced pressure. The raw compound thus resulting was purified by flash chromatography on silica gel, using as eluent a mixture of hexane:ethyl acetate in a ratio of 8:2.

Approximately 10 g of methyl of 2-(2-chlorethyl)-2H-indazole-3-carboxylate were thus obtained.

$^1$H-NMR (300 MHz, CDCl$_3$) δ: 3.9-4.1 (m, 5H); 5.24 (t, J=6.0 Hz; 2H); 7.2-7.4 (m, 2H); 7.79 (d; J=9.0 Hz; 1H); 8.02 (d; J=9.0 Hz; 1H).

1b) Methyl of 2-(2-azidoethyl)-2H-indazole-3-carboxylate

Sodium azide (8.8 g; 0.135 mol) was added to a solution of methyl of 2-(2-azidoethyl)-2H-indazole-3-carboxylate (9 g, 0.038 mol) in dimethyl sulphoxide (DMSO) (100 ml) under strong stirring at room temperature.

The reaction mixture was then processed by cooling it to room temperature, diluting it with water (100 ml) and extracting it several times with ethyl acetate (3×100 ml). The organic phases collected together were washed with water (3×25 ml), then with a saturated solution of NaCl (30 ml) and, at the end, dried with anhydrous Na$_2$SO$_4$. The solvent was removed by evaporation at reduced pressure thus obtaining about 6 g of methyl of 2-(2-azidoethyl)-2H-indazol-3-carboxylate, which was used for subsequent reactions without further purification steps.

$^1$H-NMR (300 MHz, CDCl$_3$) δ: 3.87 (t, J=6.0 Hz; 2H); 4.04 (s, 3H); 5.11 (t, J=6.0 Hz; 2H); 7.2-7.4 (m, 2H); 7.80 (t, J=9.0 Hz; 1H); 8.01 (d; J=9.0 Hz; 1H).

1c) 3,4-dihydropyrazino[1,2-b]indazol-1(2H)-one

A suspension containing methyl of 2-(2-azidoethyl)-2H-indazol-3-carboxylate (6 g; 0.024 mol), 10% palladium on charcoal (0.5 g; 0.5 mmol) in 5N hydrochloride ethanol (100 ml) was put in a Parr system to hydrogenize under hydrogen atmosphere at room temperature for 24 h.

Once the reaction was over, the suspension was filtered on celite and the solvent was removed by evaporation at reduced pressure.

The raw product thus obtained was dissolved in absolute ethanol (250 ml), added with triethylamine (12 ml; 0.12 mol) and stirred under reflux for 48 h. The reaction was then stopped by removing the solvent by evaporation at reduced pressure. The residue was taken up with water (100 ml) and extracted with dichloromethane (DCM) (3×150 ml). The organic phase collected together were then washed with a saturated solution of NaCl (50 ml) and dried with anhydrous Na$_2$SO$_4$. About 3 g of raw product were obtained. This was purified by flash chromatography on silica gel, using as eluent a mixture of hexane:ethyl acetate in a ratio of 8:2. Thus, 1.5 g of 3,4-dihydropyrazino[1,2-b]indazol-1(2H)-one were obtained.

$^1$H-NMR (300 MHz, CDCl$_3$) δ: 3.6-3.8 (m, 2H); 4.64 (t, J=6.0 Hz; 2H); 7.26 (t, J=9.0 Hz; 1H); 7.36 (t, J=9.0 Hz; 1H); 7.75 (d, J=9.0 Hz; 1H); 7.98 (d; J=9.0 Hz; 1H).

1d) Tert-butyl 4-[(1-oxo-3,4-dihydropyrazino[1,2-b]indazol-2(1H)-yl)methyl]piperidine-1-carboxilate 60% NaH (0.72 g; 0.018 mol) was added to a solution of 3,4-dihydropyrazino[1,2-b]indazol-1(2H)-one (2.7 g; 0.015 mol) in dimethylformamide (DMF) (50 ml) kept stirred at room temperature.

The reaction mixture was kept stirred at the same temperature under nitrogen atmosphere for 2 h 30', then a solution of tert-butyl 4-{[(methylsulphonyl)oxy]methyl}piperidine-1-carboxylate (4.4 g; 0.015 mol) in DMF (25 ml) was added slowly. Once the additions were over, the mixture was warmed at 150° C. for 6 h. The reaction was then stopped by cooling the mixture at room temperature and by removing the solvent by evaporation at reduced pressure. The residue was taken up with dichloromethane and then filtered through a silica gel pad. The solvent was removed by evaporation at reduced pressure, thus obtaining 3.5 g of tert-butyl 4-[(1-oxo-3,4-dihydropyrazino[1,2-b]indazol-2(1H)-yl)methyl]piperidine-1-carboxylate, used in the subsequent reactions without further purification steps.

$^1$H-NMR (300 MHz, CDCl$_3$) δ: 1.1-1.4 (m, 2H); 1.45 (s, 9H); 1.6-1.8 (m, 2H); 1.9-2.1 (m, 1H); 2.71 (bt, J=13.2 Hz; 2H); 3.4-3.6 (m, 2H); 3.89 (t, J=6.6 Hz, 2H); 4.0-4.3 (m, 2H); 4.69 (t, J=6.6 Hz; 2H); 7.2-7.4 (m, 2H); 7.75 (d, J=8.7 Hz; 1H); 8.16 (d, J=8.7 Hz; 1H).

1e) 2-(piperidin-4-ylmethyl)-3,4-dihydropyrazino[1,2-b]indazol-1(2H)-one hydrochloride A solution containing tert-butyl 4-[(1-oxo-3,4-dihydropyrazino[1,2-b]indazol-2(1H)yl)methyl]piperidine-1-carboxylate (3.5 g; 0.009 mol), ethyl acetate (20 ml) and 3M hydrochloric ethanol (10 ml) was kept stirred at room temperature for 2 h. The reaction was then stopped by filtering the solid that had formed and washing it with ethyl acetate. Thus, 1.5 g of 2-(piperidin-4-ylmethyl)-3,4-dihydropyrazino[1,2-b]indazol-1(2H)-one hydrochloride were obtained, that was used for the subsequent reaction without further purification steps.

$^1$H-NMR (300 MHz, DMSO-d6+D$_2$O) δ: 1.38 (bq, J=9.0 Hz; 2H); 1.81 (bd, J=12.0 Hz; 2H); 1.9-2.1 (m, 1H); 2.80 (bt, J=9.0 Hz; 2H); 3.25 (bd, J=12.0 Hz; 2H); 3.42 (d, J=6.0 Hz; 2H); 3.81 (t, J=6.0 Hz; 2H); 4.74 (t, J=6 Hz; 2H); 7.27 (t, J=9.0 Hz; 1H); 7.36 (t, J=9.0 Hz; 1H); 7.75 (d, J=9.0 Hz; 1H); 8.00 (d, J=9.0 Hz; 1H).

1f) 2-({1-[2-(4-fluorophenyl)ethyl]piperidin-4-yl}methyl)-3,4-dihydropyrazino[1,2-b]indazol-1(2H)-one hydrochloride A solution containing 2-(piperidin-4-yl-methyl)-3,4-dihydropyrazino[1,2-b]indazol-1(2H)-one hydrochloride (528 mg; 1.64 mmol), potassium carbonate (610 mg; 4.4 mmol), 4-fluorophenethyl bromide (450 mg; 2.2 mmol) in ethanol (10 ml) was kept stirred under reflux for 24 h. The reaction was then stopped by cooling the mixture at room temperature and concentrating the solvent under reduced pressure. The residue was taken up with DCM (30 ml) and washed respectively with a saturated solution of NaHCO$_3$ (2×20 ml), water (2×15 ml) and a saturated solution of NaCl (10 ml). The organic phase was then dried with Na$_2$SO$_4$ and the solvent was removed by evaporation at reduced pressure. The solid raw product was then purified by flash chromatography on silica gel, using as eluent a mixture of chloroform:methanol in a ratio of 9:1. The product thus purified was dissolved in a mixture of diethyl ether:ethanol in a ratio of 10:1 (10 ml) and treated at room temperature with 3M hydrochloric ethanol (0.33 ml). The solid thus formed was filtered and crystallized by a mixture isopropanol:diisopropyl ether in a ratio of 3:7. Thus, 250 mg of 2-({1-[2-(4-fluorophenyl)ethyl]piperidin-4-yl}methyl)-3,4-dihydropyrazino[1,2-b]-indazol-1(2H)-one hydrochloride were obtained.

$^1$H-NMR (300 MHz, DMSO-d6) δ: 1.49-1.78 (m, 2H); 1.81-2.10 (m, 3H); 2.76-2.99 (m, 2H); 3.00-3.12 (m, 2H); 3.17-3.40 (m, 2H); 3.47 (d, J=6.61 Hz; 2H); 3.51-3.67 (m, 2H); 3.93 (t, J=6.11 Hz; 2H); 4.75 (t, J=6.11 Hz; 2H); 7.11-7.42 (m, 6H); 7.76 (dt, J=8.59 Hz; J=0.99 Hz; 1H); 8.01 (dt, J=8.26 Hz; J=1.16 Hz; 1H), 10.51 (bs, 1H).

Example 2

2-({1-[2-(4-fluorophenyl)ethyl]piperidin-3-yl}methyl)-3,4-dihydropyrazino[1,2-b]indazol-1(2H)-one 2a) Tert-butyl-2-bromoethylcarbamate Triethylamine (2.02 g; 0.020 mol) was added drop wise to a solution of 2-bromoethanamine (2.04 g; 0.010 mol) and tert-butoxycarbonyl anhydride (1.74 g; 0.010 mol) in dichloromethane (50 ml), kept under stirring at 0° C. The reaction was kept stirred for 15 minutes at 0° C., then for 8 h at room temperature. The mixture was washed with water (2×50 ml) and the organic phase was dried on Na$_2$SO$_4$. After removing the solvent by evaporation at reduced pressure, the residue was purified by flash chromatography on silica gel, using as eluent a mixture of hexane:ethylacetate in a ratio of 8:2. Thus, 1.79 g of tert-butyl-2-bromoethyl-carbamate were obtained. This solid was used for the subsequent reaction without further purification steps.

$^1$H-NMR (200 MHz, CDCl$_3$) δ: 1.41 (s, 9H); 3.24-3.59 (m, 4H); 4.95 (bs, 1H).

2b) Methyl 2-[2-(tert-butoxycarbonylamino)ethyl]-2H-indazol-3-carboxylate

Caesium carbonate (19.5 g; 0.06 mol) was added to a solution of methyl 1H-indazole-3-carboxylate (3.5 g; 0.02 mol) and of tert-butyl-2-bromoethylcarbamate (8.9 g; 0.04 mol) in DMF (30 ml), kept under stirring at room temperature. The mixture was kept under strong stirring at room temperature for 48 h, then was processed by adding water (50 ml) and, successively, 1M HCl until a pH of 6 was obtained.

The aqueous phase was extracted by ethyl acetate (3×50 ml) and the organic phases collected together were washed with a saturated solution of NaCl (10 ml), then dried on Na$_2$SO$_4$. After removing the solvent by evaporation at reduced pressure, the residue was purified by flash chromatography on silica gel; using as eluent a mixture of hexane:ethyl acetate in a ratio of 6:4. Thus, 2.87 g of methyl 2-[2-(tert-butoxycarbonylamino)ethyl]-2H-indazole-3-carboxylate were obtained, used for subsequent reaction without further purification steps.

$^1$H-NMR (200 MHz, CDCl$_3$) δ: 1.36 (s, 9H); 3.74 (q, 2H, J=5.5 Hz); 4.03 (s, 3H); 4.89-5.07 (bs, 1H); 5.03 (t, 2H, J=5.5 Hz); 7.23-7.42 (m, 2H); 7.79 (dt, 1H, J=7.5 Hz; J=1.6 Hz); 8.02 (dt, 1H, J=7.5 Hz; J=1.6 Hz).

2c) 3,4-dihydropyrazino[1,2-b]indazol-1(2H)-one

A solution of 1.25M HCl in ethanol (48 ml; 0.06 mol) was added slowly to a solution of methyl 2-[2-(tert-butoxycarbonylamine)ethyl]-2H-indazole-3-carboxylate (6.38 g; 0.02 mol) in ethyl acetate (50 ml) kept stirred at room temperature. The mixture thus obtained was kept under stirring at room temperature for 2 h. The solvent was then removed by evaporation at reduced pressure and the residue was treated with ethyle acetate (20 ml) at room temperature and filtered. The solid thus obtained was dissolved in methanol (10 ml) and caesium carbonate (13.0 g; 0.04 mol) was added to the resultant solution, kept stirred at room temperature. The mixture was kept under stirring for 16 h at room temperature, then the solvent was removed by evaporation at reduced pressure. The residue was taken up with water (50 ml) and the aqueous phase was extracted several times with ethyl acetate (5×50 ml). The organic phases collected together were dried on Na$_2$SO$_4$ and about 4 g of raw product were obtained after the solvent was removed by evaporation at reduced pressure. The raw product was then purified by flash chromatography on silica gel, using a mixture of hexane:ethyl acetate in a ratio of 8:2 as eluent. Thus, 3.4 g of 3,4-dihydropyrazino[1,2-b]indazol-1(2H)-one were obtained.

$^1$H-NMR (200 MHz, CDCl$_3$) δ: 3.93 (dt, 2H, J=6.7 Hz; J=1.7 Hz); 4.72 (t, 2H, J=6.7 Hz); 6.35 (bs, 1H); 7.27-7.46 (m, 2H); 7.78 (dt, 1H, J=8.4 Hz; J=1.4 Hz); 8.16 (dt, 1H, J=8.4 Hz; J=1.4 Hz).

2d) Tert-butyl 3-[(1-oxo-3,4-dihydropyrazino[1,2-b]indazol-2(1H)-yl)-methyl]piperidine-1-carboxylate The product was prepared following the method described in example 1d), but using tert-butyl 3-{[(methylsulphonyl)oxy]methyl}-piperidine-1-carboxylate as reagent. Thus, 3.8 g of tert-butyl 3-[(1-oxo-3,4-dihydropyrazino[1,2-b]indazol-2(1H)-yl)methyl]piperidine-1-carboxylate were obtained.

$^1$H-NMR (200 MHz, CDCl$_3$) δ: 1.20-1.45 (m, 1H); 1.43 (s, 3H); 1.55-2.10 (m, 4H); 2.65-3.05 (m, 2H); 3.30-3.75 (m, 2H); 3.75-4.05 (m, 2H); 3.90 (t, 2H, J=6.1 Hz); 4.72 (t, 2H, J=6.1 Hz); 7.25-7.45 (m, 2H); 7.76 (dt, 1H, J=8.4 Hz; J=1.1 Hz); 8.15 (dt, 1H, J=8.0 Hz; J=1.3 Hz).

2e) 2-({1-[2-(4-fluorophenyl)ethyl]piperidin-3-yl}methyl)-3,4-dihydropyrazino[1,2-b]indazol-1(2H)-one A solution of 1.25M HCl in ethanol (4.8 ml; 0.006 mol) was added to a solution containing tert-butyl 3-[(1-oxo-3,4-dihydropyrazino[1,2-b]indazol-2(1H)-yl)methyl]piperidine-1-carboxylate (0.77 g; 0.002 mol) in ethyl acetate (7 ml), kept stirred at room temperature.

The mixture thus obtained was kept under stirring at room temperature for 2 h, then the solvent was removed by evaporation at reduced pressure. The residue thus obtained was taken up with ethyl acetate (5 ml) and filtered. The solid product was dissolved with 1-(2-bromoethyl)-4-fluorobenzene (0.81 g; 0.004 mol) in anhydrous DMF (10 ml). Caesium carbonate (1.95 g; 0.006 mol) was added to the resultant solution, kept stirred at room temperature. The mixture was then kept under strong stirring at room temperature for 48 h and then was processed by adding water (20 ml) and ethyl acetate (25 ml). The aqueous phase was extracted several times with ethyl acetate (3×20 ml) and the organic phases collected together were dried on Na$_2$SO$_4$. The solvent was then removed by evaporation at reduce pressure and the residue was purified by flash chromatography on silica gel, using a mixture of hexane:ethyl acetate in a ratio of 7:3 as eluent.

Thus, 170 mg of 2-({1-[2-(4-fluorophenyl)ethyl]piperidin-3-yl}methyl)-3,4-dihydropyrazino[1,2-b]indazol-1(2H)-one were obtained.

$^1$H-NMR (300 MHz, DMSO-d6) δ: 8.00 (d, J=8.48 Hz; 1H), 7.75 (d, J=8.77 Hz; 1H); 7.31-7.41 (m, 1H); 7.18-7.30 (m, 3H); 6.99-7.11 (m, 2H); 4.70 (t, J=6.14 Hz; 2H), 3.88 (t, J=6.14 Hz; 2H), 3.32-3.56 (m, 2H); 2.63-2.86 (m, 4H); 2.39-2.47 (m, 2H); 1.79-2.11 (m, 3H); 1.67 (d, J=10.23 Hz; 2H); 1.35-1.53 (m, 1H); 1.03 (d, J=9.35 Hz; 1H).

Example 5

2-({1-[2-(2-fluorophenyl)ethyl]piperidin-3-yl}methyl)-3,4-dihydropyrazino[1,2-b]indazol-1(2H)-one hydrochloride The product was prepared following the method described in example 2e), but using 1-(2-bromoethyl)-2-fluorobenzene as reagent. The desired product was purified by flash chromatography on silica gel, using a mixture of chloroform:methanol in a ratio of 9:1 as eluent.

Thus, 350 mg of 2-({1-[2-(2-fluorophenyl)ethyl]piperidin-3-yl}methyl)-3,4-dihydropyrazino[1,2-b]indazol-1(2H)-one hydrochloride were obtained.

$^1$H-NMR (300 MHz, DMSO-d6) δ: 10.81 (bs, 1H); 8.00 (dt, J=1.16; 8.26 Hz; 1H); 7.76 (d, J=8.59 Hz; 1H); 7.09-7.42 (m, 6H); 4.71-4.81 (m, 2H); 3.93 (t, J=6.28 Hz; 2H); 3.48-3.70 (m, 3H); 3.06-3.46 (m, 5H); 2.67-3.00 (m, 2H); 2.36-2.47 (m, 1H); 1.66-2.05 (m, 3H); 1.05-1.39 (m, 1H).

Example 8

2-({1-[2-(2-fluorophenyl)ethyl]piperidin-4-yl}methyl)-3,4-dihydropyrazino[1,2-b]indazol-1(2H)-one The product was prepared following the method described in example 2e), but using tert-butyl 4-[(1-oxo-3,4-dihydropyrazino[1,2-b]indazol-2(1H)-yl)methyl]piperidine-1-carboxylate (prepared in example 1d) and 1-(2-bromoethyl)-2-fluorobenzene as reagents. The desired product was purified by flash chromatography on silica gel, using a mixture of chloroform:methanol in a ratio of 95:5 as eluent.

Thus, 160 mg of 2-({1-[2-(2-fluorophenyl)ethyl]piperidin-4-yl}methyl)-3,4-dihydropyrazino[1,2-b]indazol-1(2H)-one were obtained.

$^1$H-NMR (300 MHz, DMSO-d6) δ: 8.00 (d, J=8.18 Hz; 1H); 7.74 (d, J=8.48 Hz; 1H); 7.17-7.41 (m, 4H); 7.05-7.16 (m, 2H); 4.70 (t, J=6.30 Hz; 2H); 3.90 (t, J=6.30 Hz; 2H); 3.41 (d, J=7.02 Hz; 2H); 2.91 (d, J=10.52 Hz; 2H); 2.76 (t, J=7.50 Hz; 2H), 1.86-2.06 (m, 2H); 1.55-1.83 (m, 3H); 1.12-1.37 (m, 2H).

Example 10

2-({1-[2-(4-fluorophenyl)ethyl]piperidin-3-yl}methyl)-2,3,4,5-tetrahydro-1H-[1,4]diazepino[1,2-b]indazol-1-one dihydrochloride

10a) tert-butyl-3-bromopropylcarbamate

The product was prepared using the method described in example 2a), using 3-bromopropan-1-amine as reagent. The product was purified by flash chromatography on silica gel, using a mixture of hexane:ethyl acetate in a ratio of 95:5 as eluent. Thus, 1.77 g of tert-butyl-3-bromopropylcarbamate were obtained.

$^1$H-NMR (200 MHz, CDCl$_3$) δ: 1.41 (s, 9H); 2.02 (qn, 2H, J=6.5 Hz); 3.24 (t, 2H, J=6.5 Hz); 3.41 (t, 2H, J=6.5); 4.7 (bs, 1H).

10b) Methyl 2-[3-(tert-butoxycarbonylamine)propyl]-2H-indazol-3-carboxylate

The product was prepared using the method described in example 2b), using tert-butyl-3-bromopropylcarbamate as reagent. The product was purified by flash chromatography on silica gel, using a mixture of hexane:ethyl acetate in a ratio of 7:3 as eluent.

Thus, 3.13 g of methyl 2-[3-(tert-butoxycarbonylamine)propyl]-2H-indazol-3-carboxylate were obtained.

$^1$H-NMR (200 MHz, CDCl$_3$) δ: 1.43 (s, 9H); 2.16 (qn, 2H, J=6.5 Hz); 3.10 (q, 2H, J=6.5 Hz); 4.03 (s, 3H); 4.97 (t, 2H, J=6.5 Hz); 4.90-5.10 (bs, 1H); 7.20-7.40 (m, 2H); 7.76 (dt, 1H, J=8.3 Hz; J=1.1 Hz); 8.01 (dt, 1H, J=7.3 Hz; J=1.3 Hz).

10c) 2,3,4,5-tetrahydro-1H-[1,4]diazepino[(1,2-b]indazol-1-one

The product was prepared using the method described in example 2c), using methyl 2-[3-(tert-butoxycarbonylamine)propyl]-2H-indazol-3-carboxylate as reagent. The product was purified by flash chromatography on silica gel, using a mixture of pentane:diethyl ether in a ratio of 95:5 as eluent. Thus, 3.5 g of 2,3,4,5-tetrahydro-1H-[1,4]diazepino[1,2-b]indazol-1-one were obtained.

$^1$H-NMR (200 MHz, CDCl$_3$) δ: 2.42 (qn, 2H, J=6.6 Hz); 3.43 (q, 2H, J=6.6 Hz); 4.82 (t, 2H, J=6.6 Hz); 6.38 (bs, 1H); 7.20-7.45 (m, 2H); 7.74 (dt, 1H, J=8.4 Hz; J=1.2 Hz); 8.06 (dt, 1H, J=8.4 Hz; J=1.4 Hz).

10d) Tert-butyl 3-[(1-oxo-4,5-dihydro-1H-[1,4]diazepino[1,2-b]indazol-2(3H)-yl)methyl]piperidine-1-carboxylate The product was prepared using the method described in example 1d), using 2,3,4,5-tetrahydro-1H-[1,4]diazepino[1,2-b]indazol-1-one and tert-butyl 3-{[(methylsulphonyl)oxy]methyl}piperidine-1-carboxylate as reagents. Thus, 3.6 g of tert-butyl 3-[(1-oxo-4,5-dihydro-1H-[1,4]diazepino[1,2-b]indazol-2(3H)-yl)methyl]piperidine-1-carboxylate were obtained.

$^1$H-NMR (200 MHz, CDCl$_3$) δ: 1.15-1.40 (m, 1H); 1.44 (s, 3H); 1.50-2.10 (m, 4H); 2.45 (qn, 2H, J=6.7 Hz); 2.55-2.95 (m, 2H); 3.40-3.70 (m, 1H); 3.45 (t, 2H, J=6.7 Hz); 3.80-4.15 (m, 3H); 4.77 (t, 2H, J=6.7 Hz); 7.15-7.40 (m, 2H); 7.72 (dt, 1H, J=8.6 Hz; J=1.0 Hz); 7.94 (dt, 1H, J=8.3 Hz; J=1.2 Hz).

10e) 2-({1-[2-(4-fluorophenyl)ethyl]piperidin-3-yl}methyl)-2,3,4,5-tetrahydro-1H-[1,4]diazepino[1,2-b]indazol-1-one dihydrochloride The product was prepared using the method described in example 2e), using tert-butyl 3-[(1-oxo-4,5-dihydro-1H-[1,4]diazepino[1,2-b]indazol-2(3H)-yl)methyl]piperidine-1-carboxylate as reagent. The amine product was purified by flash chromatography on silica gel, using a mixture of chloroform:methanol in a ratio on 9:1 as eluent. The purified product was dissolved in a mixture of diethyl ether:ethanol in a ratio of 10:1 (10 ml) and was processed at room temperature with 3M HCl in ethanol (0.33 ml). The solid thus formed was filtered and crystallized from a mixture of isopropanol:diisopropyl ether in a ratio of 8:2. Thus, 188 mg of 2-({1-[2-(4-fluorophenyl)ethyl]piperidin-3-yl}methyl)-2,3,4,5-tetrahydro-1H-[1,4]diazepino[1,2-b]indazol-1-one dihydrochloride.

$^1$H-NMR (300 MHz, DMSO-d6) δ: 11.24 (bs, 1H); 10.96 (bs, 1H); 7.79-7.86 (m, 1H); 7.70 (d, J=8.59 Hz; 1H); 7.25-7.41 (m, 3H); 7.01-7.25 (m, 3H); 4.64-4.88 (m, 2H); 3.00-3.85 (m, 10H); 2.67-2.97 (m, 2H); 2.53-2.65 (m, 1H); 2.24-2.43 (m, 1H); 1.80-2.04 (m, 3H); 1.14-1.39 (m, 1H).

Example 13

2-({1-[2-(2-fluorophenyl)ethyl]piperidin-3-yl}methyl)-2,3,4,5-tetrahydro-1H-[1,4]diazepino[1,2-b]indazol-1-one dihydrochloride The product was prepared using the method described in example 10e), using 1-(2-bromoethyl)-2-fluorobenzene as reagent. The amine product was purified by flash chromatography on silica gel, using a mixture of chloroform:methanol in a ratio on 9:1 as eluent. The final product was instead purified by crystallization from a mixture of isopropanol:diisopropyl ether in a ratio of 8:2. Thus, 163 mg of 2-({1-[2-(2-fluorophenyl)ethyl]piperidin-3-yl}methyl)-2,3,4,5-tetrahydro-1H-[1,4]diazepino[1,2-b]indazol-1-one dihydrochloride were obtained.

$^1$H-NMR (300 MHz, DMSO-d6) δ: 11.19 (bs, 1H); 10.40 (bs, 1H); 7.83 (d, J=8.26 Hz; 1H); 7.70 (d, J=8.92 Hz; 1H); 7.25-7.45 (m, 3H); 7.11-7.24 (m, 3H); 4.59-4.91 (m, 2H); 3.04-3.86 (m, 10H); 2.68-3.04 (m, 2H); 2.54-2.63 (m, 1H); 2.21-2.44 (m, 1H); 1.79-2.05 (m, 3H); 1.15-1.37 (m, 1H).

Example 16

2-({1-[2-(4-fluorophenyl)ethyl]piperidin-4-yl}methyl)-2,3,4,5-tetrahydro-1H-[1,4]diazepino[1,2-b]indazol-1-one hydrochloride

16a) Tert-butyl 4-((1-oxo-4,5-dihydro-1H-[1,4]diazepino[1,2-b]indazol-2(3H)-yl)methyl)piperidine-1-carboxylate The product was prepared using the method described in example 1d), using 2,3,4,5-tetrahydro-1H-[1,4]diazepino[1,2-b]indazol-1-one as reagent. The product was purified by flash chromatography on silica gel, using the mixture of pentane:diethyl ether in a ratio on 95:5 as eluent. Thus, 3.40 g of tert-butyl 4-((1-oxo-4,5-dihydro-1H-[1,4]diazepino[1,2-b]indazol-2(3H)-yl)methyl)piperidine-1-carboxylate were obtained.

$^1$H-NMR (200 MHz, CDCl$_3$) δ: 2.41 (s, 3H); 7.26 (d, 2H, J=8.1 Hz); 7.45 (d, 2H, J=8.1 Hz); 7.57 (d, 1H, J=13.6 Hz); 7.99 (d, 1H, J=13.6 Hz).

16b) 2-({1-[2-(4-fluorophenyl)ethyl]piperidin-4-yl}methyl)-2,3,4,5-tetrahydro-1H-[1,4]diazepino[1,2-b]indazol-1-one hydrochloride The product was prepared using the method described in example 10e), using tert-butyl 4-[(1-oxo-4,5-dihydro-1H-[1,4]diazepino[1,2-b]indazol-2(3H)-yl)methyl]piperidine-1-carboxylate as reagent. The amine product was purified by flash chromatography on silica gel, using the mixture chlorofom:methanol in a ratio of 95:5 as eluent. The final product was instead purified from a mixture of isopropanol:diisopropyl ether in a ratio of 4:6. Thus, 167 mg of 2-({1-[2-(4-fluorophenyl)ethyl]piperidin-4-yl}methyl)-2,3,4,5-tetrahydro-1H-[1,4]diazepino[1,2-b]indazol-1-one hydrochloride were obtained.

$^1$H-NMR (300 MHz, DMSO-d6) δ: 10.63 (bs, 1H); 7.82 (d, J=8.59 Hz; 1H), 7.70 (d, J=8.92 Hz; 1H); 7.25-7.40 (m, 3H); 7.10-7.25 (m, 3H); 4.72 (t, J=6.94 Hz; 2H); 3.45-3.70 (m, 4H); 3.43 (t, J=6.44 Hz; 2H); 2.75-3.35 (m, 7H); 2.37 (q, J=6.69 Hz; 2H); 1.85-2.10 (m, 3H); 1.50-1.85 (m, 2H).

Example 17

2-({1-[2-(4-fluorophenyl)ethyl]piperidin-4-yl}methyl)-3,4,7,8,9,10-esahydropyrazino[1,2-b]indazol-1(2H)-one hydrochloride

17a) Tert-butyl 4-[(1-oxo-3,4,7,8,9,10-esahydropyrazino[1,2-b]indazol-2(1H)-yl)methyl]piperidine-1-carboxylate The product was prepared using the method described in example 1d), using 3,4,7,8,9,10-esahydropyrazino[1,2-b]indazol-1(2H)-one as a reagent. The raw product was used for the subsequent reaction without further purification steps.

$^1$H-NMR (300 MHz, DMSO-d6) δ: 4.17-4.28 (m, 2H); 3.92 (d, J=12.86 Hz; 2H); 3.66-3.77 (m, 2H); 3.26-3.35 (m, 2H); 2.59-2.72 (m, 4H); 2.55 (t, J=5.85 Hz; 2H); 1.77-1.93 (m, 1H); 1.53-1.76 (m, 6H); 1.39 (s, 9H); 1.02 (dd, 2H).

17b) 2-({1-[2-(4-fluorophenyl)ethyl]piperidin-4-yl}methyl)-3,4,7,8,9,10-esahydropyrazino[1,2-b]indazol-1(2H)-one hydrochloride The product was prepared using the method described in example 2e), using tert-butyl 4-[(1-oxo-3,4,7,8,9,10-esahydropyrazino[1,2-b]indazol-2(1H)-yl)methyl]piperidine-1-carboxylate as a reagent. The product was purified by crystallization from a mixture of isopropanol:diisopropyl ether. Thus, 0.2 g of 2-({1-[2-(4-fluorophenyl)ethyl]piperidin-4-yl}methyl)-3,4,7,8,9,10-esahydropyrazino[1,2-b]indazol-1(2H)-one hydrochloride were obtained.

$^1$H-NMR (300 MHz, DMSO-d6) δ: 10.47 (bs, 1H); 7.26-7.40 (m, 2H); 7.10-7.23 (m, 2H); 4.19-4.32 (m, 2H); 3.73 (t, J=5.95 Hz, 2H); 3.46-3.59 (m, 2H); 3.35 (d, J=6.61 Hz; 2H); 3.12-3.27 (m, 2H); 2.98-3.11 (m, 2H); 2.77-2.96 (m, 2H); 2.65 (t, J=5.78 Hz; 2H); 2.56 (t, J=5.78 Hz; 2H); 1.44-2.05 (m, 9H).

Example 20

2-[(1-phenethylpiperidin-4-yl)methyl]-3,4-dihydropyrazino[1,2-b]indazol-1(2H)-one hydrochloride The product was prepared using the method described in example 10e), using tert-butyl 4-[(1-oxo-3,4-dihydropyrazino[1,2-b]indazol-2(1H)-yl)methyl]piperidine-1-carboxylate (example 1d) and phenethyl bromide as reagents. The amine product was purified by flash chromatography on silica gel, using the mixture chloroform:methanol in a ratio of 85:15 as eluent. The final product was instead purified by crystallization from a mixture of isopropanol:diisopropyl ether in a ratio of 3:7. Thus, 121 mg of 2-[(1-phenethylpiperidin-4-yl)methyl]-3,4-dihydropyrazino[1,2-b]indazol-1(2H)-one hydrochloride were obtained.

$^1$H-NMR (300 MHz, DMSO-d6) δ: 10.84 (bs, 1H); 8.01 (d, J=8.26 Hz; 1H); 7.76 (d, J=8.59 Hz; 1H); 7.13-7.44 (m, 7H); 4.75 (t, J=6.11 Hz; 2H); 3.94 (t, J=6.11 Hz; 2H), 3.51-3.67 (m, 2H); 3.47 (d, J=6.94 Hz; 2H); 3.01-3.39 (m, 6H); 2.78-3.02 (m, 2H); 1.81-2.28 (m, 3H); 1.53-1.79 (m, 2H).

Example 22

2-[(1-phenethylpiperidin-4-yl)methyl]-2,3,4,5-tetrahydro-1H-[1,4]diazepino[1,2-b]indazol-1-one The product was prepared using the method described in example 2e), using tert-butyl 4-[(1-oxo-4,5-dihydro-1H-[1,4]diazepino[1,2-b]indazol-2(3H)-yl)methyl]piperidine-1-carboxylate (example 16a) and phenethyl bromide as reagents. The product was purified by flash chromatography on silica gel, using the mixture chloroform:methanol in a ratio of 95:5 as eluent. Thus, 223 mg of 2-[(1-phenethylpiperidin-4-yl)methyl]-2,3,4,5-tetrahydro-1H-[1,4]diazepino[1,2-b]indazol-1-one were obtained.

$^1$H-NMR (300 MHz, DMSO-d6) δ: 7.82 (d, J=8.18 Hz; 1H); 7.69 (d, J=8.48 Hz; 1H); 7.07-7.40 (m, 7H); 4.68 (t, J=7.02 Hz; 2H); 3.34-3.55 (m, 4H); 2.94 (d, J=11.40 Hz; 2H); 2.65-2.79 (m, 2H); 2.33 (qn, J=6.65 Hz; 2H); 1.97 (t, J=10.82 Hz; 2H); 1.59-1.83 (m, 3H); 1.15-1.37 (m, 2H).

Example 25

2-{[1-(phenylacetyl)piperidin-4-yl]methyl}-3,4-dihydropyrazino[1,2-b]indazol-1(2H)-one The product was prepared using the method described in example 2e), using tert-butyl 4-[(1-oxo-3,4-dihydropyrazino[1,2-b]indazol-2(1H)-yl)methyl]piperidine-1-carboxylate (example 1d) and benzeneacetyl chloride as reagents. The product was purified by flash chromatography on silica gel, using the mixture chloroform:methanol in a ratio of 9:1 as eluent. Thus, 104 mg of 2-{[1-(phenylacetyl)piperidin-4-yl]methyl}-3,4-dihydropyrazino[1,2-b]indazol-1(2H)-one were obtained.

$^1$H-NMR (200 MHz, CDCl$_3$) δ: 0.85-1.15 (m, 1H); 1.15-1.35 (m, 1H); 1.85-2.15 (m, 1H); 2.61 (td, 1H, J=13.2 Hz; J=2.8 Hz); 2.95 (td, 1H, J=13.2 Hz; J=2.8 Hz); 3.39 (dd, 1H, J=13.7 Hz; J=6.9 Hz); 3.54 (dd, 1H, J=13.7 Hz; J=7.5 Hz); 3.73 (s, 2H); 3.75-4.05 (m, 2H); 3.84 (t, 2H, J=6.3 Hz); 3.86 (d, 2H, J=6.3 Hz); 4.67 (t, 2H, J=6.3 Hz); 7.10-7.45 (m, 7H); 7.76 (dt, 1H, J=8.3 Hz; J=1.1 Hz); 8.14 (dt, 1H, J=8.2 Hz; J=1.1 Hz).

Example 26

2-{[1-(phenylacetyl)piperidin-4-yl]methyl}-2,3,4,5-tetrahydro-1H-[1,4]diazepino[1,2-b]indazol-1-one The product was prepared using the method described in example 2e), using tert-butyl 4-[(1-oxo-4,5-dihydro-1H-[1,4]diazepino[1,2-b]indazol-2(3H)-yl)methyl]piperidine-1-carboxylate (example 16a) and benzeneacetyl chloride as reagents. The product was purified by flash chromatography on silica gel, using the mixture chloroform:methanol in a ratio of 9:1 as eluent. Thus, 141 mg of 2-{[1-(phenylacetyl)piperidin-4-yl]methyl}-2,3,4,5-tetrahydro-1H-[1,4]diazepino[1,2-b]indazol-1-one were obtained.

$^1$H-NMR (200 MHz, CDCl$_3$) δ: 0.85-1.45 (m, 2H); 1.85-2.15 (m, 1H); 2.39 (qn, 2H, J=6.7 Hz); 2.64 (td, 1H, J=12.5 Hz; J=2.2 Hz); 2.98 (td, 1H, J=12.5 Hz; J=2.2 Hz); 3.25-3.45 (m, 4H); 3.50-3.70 (m, 1H); 3.75 (s, 2H); 3.89 (bd, 2H, J=14.2 Hz); 4.50-4.80 (m, 2H); 4.67 (t, 2H, J=7.1 Hz); 7.10-7.45 (m, 7H); 7.72 (dt, 1H, J=8.6 Hz; J=1.1 Hz); 7.93 (dt, 1H, J=8.2 Hz; J=1.1 Hz).

Example 28

2-[3-(4-phenylpiperidin-1-yl)propyl]-3,4-dihydropyrazino[1,2-b]indazol-1(2H)-one hydrochloride 28a) 1-(3-chloropropyl)-4-phenylpiperidine Solid caesium carbonate (195 g; 0.6 mmol) was added to a solution of 4-phenylpiperidine (32 g; 0.2 mol), 1-bromo-3-chloropropane (40 ml; 0.4 mmol) in anhydrous DMF (300 ml), kept stirred at room temperature. The mixture was kept under stirring at the same temperature for 12 h. Water (1000 ml) and ethyl acetate (500 ml) were added to stop the reaction. After separating the phases, the aqueous phase was extracted several times with ethyl acetate (3×500 ml). The organic phases collected together were washed respectively with water (100 ml) and a saturated solution of NaCl (100 ml), and then dried on anhydrous Na$_2$SO$_4$. The solvent was removed by evaporation at reduced pressure and the residue was purified by flash chromatography on silica gel, using a mixture of hexane:ethyl acetate in a ratio of 1:1 as eluent. Thus, 29.5 g of 1-(3-chloropropyl)-4-phenylpiperidine were obtained as colorless oil.

$^1$H-NMR (200 MHz, CDCl$_3$) δ: 1.75-1.90 (m, 2H); 1.90-2.15 (m, 6H); 2.35-2.65 (m, 3H); 3.02 (bd, 2H, J=6.4 Hz); 3.64 (t, 2H, J=6.4 Hz); 7.05-7.45 (m, 5H).

28b) 2-[3-(4-phenylpiperidin-1-yl)propyl]-3,4-dihydropyrazino[1,2-b]indazol-1(2H)-one hydrochloride A solution of 3,4-dihydropirazyno[1,2-b]indazol-1(2H)-one (375 mg; 2.0 mmol) in a mixture of tetrahydrofuran:dimethylformamide (DMF) in a ratio of 1:1 (4 ml) was added drop wise to a suspension of NaH 55% in mineral oil (104 mg; 2.4 mmol) in anhydrous tetrahydrofuran (THF), kept stirred at room temperature under argon atmosphere. The mixture was kept under stirring at the same temperature under inert atmosphere for 1 h; then, a solution of 1-(3-chloropropyl)-4-phenylpiperidine (4.4 g; 0.015 mol) in DMF (25 ml) was slowly added. Once the additions were over, the mixture was heated at the reflux temperature for 6 h. The reaction was then stopped by cooling the mixture to room temperature and by adding ethyl acetate (10 ml). The mixture was then filtered through a silica gel pad, then the solvent was removed by evaporation at reduced pressure. The residue was purified by flash chromatography on silica gel, using a mixture of chloroform:methanol in a ratio of 9:1 as eluent. The product thus purified was dissolved in a mixture of diethyl ether:ethanol in a ratio of 10:1 (10 ml) and processed at room temperature with 3M HCl in ethanol (0.33 ml). The solid thus formed was filtered and crystallized from a mixture of isopropanol:diisopropyl ether in a ratio 1:1.

Thus, 197 mg of 2-[3-(4-phenylpiperidin-1-yl)propyl]-3,4-dihydropyrazino[1,2-b]indazol-1(2H)-one hydrochloride were obtained.

$^1$H-NMR (300 MHz, DMSO-d6) δ: 10.88 (bs, 1H); 8.02 (dt, J=1.16 Hz; J=8.26 Hz; 1H); 7.77 (dt, J=0.93 Hz; J=8.55 Hz; 1H); 7.18-7.42 (m, 7H); 4.74-4.81 (m, 2H); 3.89-4.03 (m, 2H); 3.65 (t, J=6.44 Hz; 2H); 3.57 (d, J=11.72 Hz; 2H); 2.92-3.18 (m, 4H); 2.70-2.87 (m, 1H); 2.01-2.26 (m, 4H); 1.94 (d, J=12.55 Hz; 2H).

Example 31

2-[3-(4-phenylpiperidin-1-yl)propyl]-2,3,4,5-tetrahydro-1H-[1,4]diazepino[1,2-b]indazol-1-one hydrochloride The product was prepared using the method described in example 28b), using 2,3,4,5-tetrahydro-1H-[1,4]diazepino[1,2-b]indazol-1-one (example 10c) as reagent. The amine product was purified by flash chromatography on silica gel, using a mixture of chloroform:ethanol in a ratio of 85:15 as eluent. The final product was instead purified by crystallization from a mixture of isopropanol:diisopropyl ether in a ratio of 1:1. Thus, 317 mg of 2-[3-(4-phenylpiperidin-1-yl)propyl]-2,3,4,5-tetrahydro-1H-[1,4]diazepino[1,2-b]indazol-1-one hydrochloride were obtained.

$^1$H-NMR (300 MHz, DMSO-d6) δ: 10.94 (bs, 1H); 7.84 (dt, J=1.11 Hz; J=8.34 Hz; 1H); 7.71 (dt, J=0.97 Hz; J=8.63 Hz; 1H); 7.29-7.40 (m, 3H); 7.16-7.29 (m, 4H); 4.73 (t, J=7.02 Hz; 2H); 3.55-3.73 (m, 5H); 3.44 (t, J=6.36 Hz; 2H); 2.97-3.21 (m, 4H); 2.83 (tt, J=3.63 Hz; J=12.14 Hz; 1H); 2.42 (qn, J=6.65 Hz; 2H); 2.04-2.26 (m, 4H); 1.96 (d, J=13.87 Hz; 2H).

Pharmacology

The pharmacological properties of the compounds of formula (I) according to the present invention were evaluated by the methods described in the following sections Tests A, B and C.

Test A (In Vitro)

The affinity of the compounds of formula (I) according to the present invention for the human recombinant 5-HT$_{2A}$ serotonin receptor was demonstrated by the standard methodology by Bonhaus D W, Bach C, DeSouza A, Rich Salazar F H, Matsuoka B D, Zuppan P, Chan H W and Eglen R M (1995) in "*The pharmacology and distribution of human 5-hydroxytryptamine 2B (5-HT$_{2B}$) receptor gene products: comparison with 5-HT$_{2A}$ and 5-HT$_{2C}$ receptors*". Br. J. Pharmacol. 115: 622-628.

In particular, binding to the human 5-HT$_{2A}$ serotonin receptor was performed using, as starting material, a preparation of membranes from stable recombinant CHO-K1 cell line expressing the human 5-HT$_{2A}$ receptor.

Displacement studies were conducted using 0.5 nM [$^3$H]-ketanserin as radioligand. This concentration was selected on the basis of saturation studies, which made possible to obtain a Bmax of 0.51 pmol/mg protein and a Kd of 0.2 nM.

The non-specific binding was measured in the presence of 1 µM mianserin. The assay was conducted in Tris-HCl 50 mM buffer (pH 7.4 at 37° C.), with incubation for 1 hour at 25° C. The test compounds were dissolved in DMSO, then diluted in buffer (final DMSO concentration 0.01%) and plated on 96-well plates. The compounds were tested in duplicate in an 8-points concentration response curve (in a Log scale ranging from $10^{-12}$ to $10^{-5}$ M). Ketanserin was used as reference compound.

After incubation, the membranes were filtered on glass-fibre filters (GF/B) (Unifilter, Packard) treated with 0.5% polyethyleneimine. Then the filters were washed with buffer solution and oven-dried for 30 minutes at 45° C. The scintillation liquid was added to each well, and at least 16 hours later the radioactivity was measured for 1 minute using a TopCount (Packard).

The IC50 values for each compound were calculated using non-linear regression analysis (GraphPad PRISM software) and the inhibition constants Ki were determined using the equation described by Cheng Y. and Prussof W. H. (1973) "*Relationship between the inhibition constant (Ki) and the concentration of inhibitor which causes 50 percent inhibition (I50) of an enzyme reaction.*" Biochem. Pharmacol. 22: 3099-3108.

The values of the affinity of representative compounds of formula (I) according to the present invention for the 5-HT$_{2A}$ receptor are shown in Table 2, in which the affinity is greater for a higher value of pKi.

TABLE 2

| Compound (No.) | 5-HT$_{2A}$ (pKi) |
|---|---|
| 1 | 7.71 |
| 2 | 5.94 |
| 5 | 6.16 |
| 8 | 8.74 |
| 10 | 6.56 |
| 13 | 6.59 |
| 16 | 8.14 |
| 17 | 7.53 |
| 20 | 7.78 |
| 22 | 7.68 |
| 28 | 7.13 |
| 31 | 7.34 |
| Ketanserin | 9.65 |

Test B (In Vitro)

The affinity of the compounds of formula (I) according to the present invention for the 5-HT$_{2C}$ serotonin receptor was demonstrated by the standard methodology described by Wolf W. A. and Schutz J. S. (1997) in "*The serotonin 5-HT$_{2C}$ receptor is a prominent serotonin receptor in basal ganglia: evidence from functional studies on serotonin-mediated phosphoinositide hydrolysis.*" J. Neurochem. 69: 1449-1458.

In particular, binding to the human serotonin 5-HT$_{2C}$ receptor was performed using, as starting material, a preparation of membranes from stable recombinant CHO-K1 cell line expressing the human 5-HT$_{2C}$ receptor.

Displacement studies were conducted using 1 nM [$^3$H]-mesulergine as radioligand. This concentration was selected on the basis of saturation studies, which made possible to obtain a Bmax of 4.9 pmol/mg protein and a Kd of 1.1 nM.

The non-specific binding was measured in the presence of 1 µM mianserin. The assay was conducted in Tris-HCl 50 mM buffer (pH 7.4 at 37° C.), 0.1% Ascorbic Acid, 10 µM Pargyline, with incubation for 1 hour at 25° C. The test compounds were dissolved in DMSO, then diluted in buffer (final DMSO concentration 0.01%) and plated on 96-well plates The compounds were tested in duplicate in an 8-points concentration response curve (in a Log scale ranging from $10^{-12}$ to $10^{-5}$ M). SB 242084 was used as reference compound. SB 242084 is a selective 5-HT$_{2C}$ serotonin receptor antagonist manufactured and sold by Sigma-Aldrich having the following structural formula:

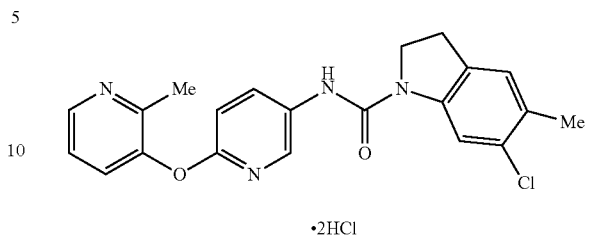

·2HCl

After incubation, the membranes were filtered on glass-fibre filters (GF/B) (Unifilter, Packard) treated with 0.5% polyethyleneimine. Then the filters were washed with buffer solution and oven-dried for 30 minutes at 45° C. The scintillation liquid was added to each well, and at least 16 hours later the radioactivity was measured for 1 minute using a TopCount (Packard).

The IC50 values for each compound were calculated using non-linear regression analysis (GraphPad PRISM software) and the inhibition constants Ki were determined using the equation described by Cheng Y. and Prussof W. H. (1973) "Relationship between the inhibition constant (Ki) and the concentration of inhibitor which causes 50 percent inhibition (I50) of an enzyme reaction." Biochem. Pharmacol. 22: 3099-3108.

The values of affinity of representative compounds of formula (I) according to the present invention for the 5-HT$_{2C}$ receptors of human recombinant cells are shown in Table 3, in which the affinity is greater for a higher value of pKi.

TABLE 3

| Compound (No.) | (h)5-HT$_{2C}$ (pKi) |
|---|---|
| 1 | 5.77 |
| 16 | <5 |
| 17 | 5.13 |
| 28 | <5 |
| 31 | <5 |
| SB 242084 | 9.33 |

The comparison between the values of affinity reported in Tables 2 and 3 above shows that the compounds of the present invention have a higher selective affinity on 5-HT$_{2A}$ receptors compared with 5-HT$_{2C}$ receptors.

Test C (In Vivo)

The interactions of the compounds of formula (I) according to the present invention with the serotoninergic system was tested following the "head twitch" model in the mouse, according to the standard methodology described by Sztanke K., Fidecka S., Kedzierska E., Karczmarzyk Z., Pihlaja K., Matosiuk D. (2005) in "*Antionociceptive activity of new imidazole carbonyl derivatives. Part 4. Synthesis and pharmacological activity of 8-aryl-3,4-dioxo-2H,8H-6,7-dihydrimidazo[2,1c][1,2,4]triazine.*" Eur. J. Med. Chem. 40: 127-134, and in Corne S. J., Pickering R. W., Warner B. T. (1963) "*A method for assessing the effects of drugs on the central actions of 5-hydroxytryptamine.*" Br. J. Pharmacol. Chemother. 20: 106-120.

The "head twitches" are a characteristic shaking of the head induced in the animals by the increase in central levels of serotonin.

Male CD-1 mice weighing 25-30 g were used for the "head twitch" test. Molecules were suspended in a 0.5% methylcellulose aqueous solution (MTC) and the animals were treated intraperitoneally with the test compounds at the dose of 5 mg/kg (10 ml/kg body weight). The control animals received the vehicle alone (MTC) by the same route. Head twitches, considered as a specific behavioural model for the activation of serotoninergic neurons, were induced by an intraperitoneal administration of 5-hydroxytryptophan (5-HTP), a precursor of serotonin (5-HT), dissolved in a 0.5% MTC solution and given at 300 mg/kg 30 min following drug administration.

The number of head twitches, which constitutes the parameter for assessment of the serotoninergic response, was measured in the interval from 24 to 26 minutes after administration of 5-HTP.

The inhibition values obtained in the "Head Twitch" test with the tested compounds are shown in FIG. 1 and in the following Table 4.

TABLE 4

| COMPOUND | % INHIBITION |
|---|---|
| 1 | 50 |
| 8 | 70 |
| 16 | 56 |
| 17 | 32 |

In particular, as shown in FIG. 1, the compounds of the invention induce a reduction in the number of head twitches ranging between 32 and 70 percent, calculated with respect to vehicle treated group, demonstrating the capacity for antagonizing the serotoninergic effects induced by administration of 5-HTP.

The invention claimed is:

1. A method for treating glaucoma, said method comprising administering, to a patient in need thereof, an effective amount of a tricyclic indazole compound of formula (I):

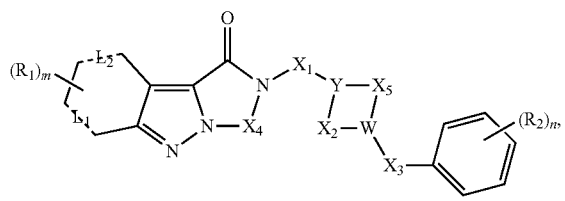

(I)

wherein:
Y is CH or N;
W is CH or N;
provided that one and only one of Y and W is a nitrogen atom;
$X_1$ is a divalent alkyl chain containing from 1 to 5 carbon atoms;
$X_3$ is a σ bond or a divalent alkyl chain containing from 1 to 5 carbon atoms;
$X_4$ is —CH$_2$—CH$_2$— or —CH$_2$—CH$_2$—CH$_2$—;
$X_2$ and $X_5$ are each independently a σ bond or a linear divalent alkyl chain containing from 1 to 4 carbon atoms, provided that the sum of carbon atoms in $X_2$ and $X_5$ is 4;
$L_1$ and $L_2$ are each a π bond;
each $R_1$ is independently H, OH, halogen, CN, $C_{1-3}$alkyl, $C_{1-3}$alkoxy, NR$^i$R$^{ii}$, NO$_2$, CF$_3$, CONR$^{iii}$R$^{iv}$, SO$_2$R$^v$, OCF$_3$, N(R$^{vi}$)SO$_2$R$^{vii}$, C(NR$^{viii}$)N(R$^{ix}$R$^x$), or N(R$^{xi}$)C(O)R$^{xii}$;
each $R_2$ is independently H, OH, halogen, CN, $C_{1-3}$alkyl, $C_{1-3}$alkoxy, $C_{1-3}$hydroxyalkyl, $C_{1-3}$aminoalkyl, NR$^i$R$^{ii}$, NO$_2$, CF$_3$, CONR$^{iii}$R$^{iv}$, SO$_2$R$^v$, OCF$_3$, N(R$^{vi}$)SO$_2$R$^{vii}$, C(NR$^{viii}$)N(R$^{ix}$R$^x$), or N(R$^{xi}$)C(O)R$^{xii}$;
m and n are each independently from 1 to 3;
R$^i$, R$^{ii}$, R$^{iii}$, R$^{iv}$, R$^v$, R$^{vi}$, R$^{vii}$, R$^{viii}$, R$^{ix}$, R$^x$, R$^{xi}$, R$^{xii}$ are each independently H or $C_{1-3}$alkyl;
or an addition salt with a pharmaceutically acceptable organic acid or a pharmaceutically acceptable inorganic acid.

2. The method of claim 1, wherein $X_1$ is a divalent alkyl chain containing from 1 to 3 carbon atoms.

3. The method of claim 1, wherein $X_3$ is a σ bond or a divalent alkyl chain containing from 1 to 3 carbon atoms.

4. The method of claim 1, wherein each $R_1$ is independently H, OH, F, Cl, CN, $C_{1-3}$alkyl group, $C_{1-3}$alkoxy group, NR$^i$R$^{ii}$ group, NO$_2$, CF$_3$, CONR$^{iii}$R$^{iv}$ group, SO$_2$R$^v$, or OCF$_3$.

5. The method of claim 1, wherein each $R_2$ is independently H, OH, F, Cl, CN, $C_{1-3}$alkyl, $C_{1-3}$alkoxy, $C_{1-3}$hydroxyalkyl, $C_{1-3}$aminoalkyl, NR$^i$R$^{ii}$, NO$_2$, CF$_3$, CONR$^{iii}$R$^{iv}$, SO$_2$R$^v$, or OCF$_3$.

6. The method of claim 1, wherein said compound or salt is an addition salt with a pharmaceutically acceptable acid selected from the group consisting of oxalic acid, maleic acid, methanesulphonic acid, paratoluenesulphonic acid, succinic acid, citric acid, tartaric acid, lactic acid, hydrochloric acid, phosphoric acid, and sulfuric acid.

* * * * *